United States Patent [19]

Thakrar et al.

[11] Patent Number: 5,158,718
[45] Date of Patent: Oct. 27, 1992

[54] CONTACT LENS CASTING

[75] Inventors: Ashok Thakrar, San Jose; Norman M. Van Houten, Cupertino; John M. Evans, Fremont, all of Calif.; Richard S. Skipper, Nr Winchester, England; Peter H. Stafford; John T. Phoenix, both of Southhampton, England

[73] Assignee: Pilkington Visioncare, Inc., Menlo Park, Calif.

[21] Appl. No.: 747,802

[22] Filed: Aug. 19, 1991

Related U.S. Application Data

[63] Continuation-in-part of Ser. No. 561,683, Aug. 2, 1990, abandoned.

[51] Int. Cl.$^5$ .............................................. B29D 11/00
[52] U.S. Cl. ..................................... 264/1.4; 264/1.7; 264/2.3; 264/2.6; 264/2.7; 264/22; 425/808
[58] Field of Search .................. 264/1.4, 1.7, 2.3, 2.7, 264/2.6, 22; 351/162; 425/174.8 E, 808; 249/134

[56] References Cited

U.S. PATENT DOCUMENTS

| | | | |
|---|---|---|---|
| 3,171,869 | 3/1965 | Weinberg | 264/1 |
| 3,294,971 | 12/1966 | Von der Heide | 250/49.5 |
| 3,419,489 | 12/1968 | Delaney | 204/312 |
| 3,526,583 | 9/1970 | Hayward | 204/165 |
| 3,661,735 | 5/1972 | Drelich | 204/165 |
| 3,668,097 | 6/1972 | Eisby | 204/165 |
| 3,854,982 | 12/1974 | Aelion et al. | 117/68 |
| 3,925,178 | 12/1975 | Gesser et al. | 204/165 |
| 4,038,165 | 7/1977 | Lowther | 204/176 |
| 4,055,378 | 10/1977 | Feneberg et al. | 351/160 |
| 4,072,769 | 2/1978 | Lidel | 427/38 |
| 4,073,577 | 2/1978 | Hofer | 351/160 |
| 4,157,892 | 6/1979 | Tanaka et al. | 8/14 |
| 4,214,014 | 7/1980 | Hofer et al. | 427/40 |
| 4,297,187 | 10/1981 | Deguchi et al. | 204/165 |
| 4,409,258 | 10/1983 | Feurer et al. | 427/38 |
| 4,445,991 | 5/1984 | Arbit | 204/168 |
| 4,457,880 | 7/1984 | Neefe | 264/1.4 |
| 4,534,723 | 8/1985 | Dillon et al. | 425/289 |
| 4,568,501 | 2/1986 | Wichterle et al. | 264/2.1 |
| 4,594,401 | 6/1986 | Takahashi et al. | 526/279 |
| 4,702,574 | 10/1987 | Bawa | 351/162 |
| 4,740,282 | 4/1988 | Gesser et al. | 204/165 |
| 4,786,444 | 11/1988 | Hwang | 264/1.4 |
| 4,836,901 | 6/1989 | Manabe et al. | 204/164 |
| 4,955,580 | 9/1990 | Seden et al. | 249/82 |

FOREIGN PATENT DOCUMENTS

| | | | |
|---|---|---|---|
| 0158999 | 4/1985 | European Pat. Off. | |
| 0362137 | 4/1990 | European Pat. Off. | 264/1.7 |

Primary Examiner—James Lowe
Attorney, Agent, or Firm—Charles E. Cates; Frank T. Barber

[57] ABSTRACT

Hydrophobic casting moulds are treated with electrical discharge, such as corona discharge, to provide enhanced compatibility with hydrophilic objects introduced into the mould, without interfering with the release properties of the mould. A preferred embodiment involves treatment of contact lens casting moulds with corona discharge to provide improvements in the lens manufacturing procedure, as well as enhancement in the quality of the contact lenses themselves. The invention is particularly applicable to the production of contact lenses having a colored iris pattern imprinted thereon.

27 Claims, 2 Drawing Sheets

CONTACT LENS CASTING

This is a continuation-in-part of copending application Ser. No. 07/561,683, filed Aug. 2, 1990 (now abandoned).

FIELD OF THE INVENTION

This invention relates to contact lens casting and in particular the treatment of contact lens casting mould to enhance the lens manufacturing procedure, and improve the quality of the contact lenses produced.

BACKGROUND AND PRIOR ART

For a number of years there has been a demand for coloured or tinted contact lenses, whether this is for identification purposes, protection of the user against bright light, or for cosmetic purposes, (not only to enhance the natural colouring of the eyes, but sometimes to conceal disfigurements).

The production of contact lenses to fulfill all the various demands, and which have a natural appearance to a viewer is demanding from a technical viewpoint and has been testing the industry for a number of years. The problems involved include the fact that colourants must be incorporated into the lens without affecting the optical properties of the final product, the colourants must resist leaching out in storage and cleaning, (including auto-claving) and must not undergo decomposition or react chemically with, or in, the presence of reagents used in daily cleaning and disinfection of the contact lens. Further they must also resist fading upon prolonged exposure to light, such as intense sunlight, and must be non-toxic and physiologically inert, as well as mechanically non-irritating.

From a commercial standpoint, it is necessary that the colouring or tinting of the contact lenses can be carried out in a cost effective manner, therefore the process used should not be so complex, time consuming or labour intensive as to be impractical.

One particular problem encountered with the production of such tinted lenses arises from the fact that the natural appearance of the human iris is not a simple solid colour, but consists of a patterned structure involving many shapes and colours which in order to provide a contact lens of natural appearance should be mimicked. Therefore, coloured lenses having a solid colour in the iris area have the disadvantage of producing an unnatural appearance when fitted in the eye.

U.S. Pat. Nos. 4,582,402 and 4,704,017 (Both Knapp) disclose coloured lens having a dot matrix pattern applied to the iris area, using offset pad printing techniques. However, in the process disclosed in these patents, the lens must first be produced, and then, in an added manufacturing segment, the pigment pattern is prepared and transferred to the surface of the previously prepared lens. Following this, the lens is subjected to further treatment to fix the pigment to the surface of the lens and render it resistant to leaching, abrasion, fading, and the like.

U.S. Pat. No. 4,668,240 discloses a process in which a colouring substance and a binding agent are printed on the surface of a contact lens in an iris simulating pattern. Here again, however, the lens must be first produced, and the printing accomplished in a series of additional steps to the manufacture.

In co-pending application Ser. No. 469,007, filed Jan. 29, 1990, now abandoned, an improved procedure is described in which the colourant is applied to the optical surface or surfaces of the casting mould in which the contact lens is to be formed. This procedure involves the use of a colouring material that is insoluble in the monomer material from which the lens is to be manufactured, dispersing the colouring material in a carrier system which is compatible with the monomer material (and may comprise the monomer from which the lens blank is to be made), and applying the dispersed colourant/carrier material on one or more surfaces of the casting mould. The basic monomeric material from which the lens is formed is introduced into the mould and contacts the surface, or surfaces, and the material is then polymerized to produce a lens blank having the coloured material impregnated in the blank, adjacent to one or both optical surfaces thereof. The procedure not only enhances the preciseness and reproducibility of the end product, but it also permits the colouring step to be incorporated as an integral part of the manufacturing process, rather than having to perform a subsequent and separate manufacturing operation.

However, in instances where the casting mould is made of a hydrophobic material, such as polyolefin, it has been difficult to apply the pigment dispersion to the mould surfaces, particularly in circumstances where the pigment carrier is a hydrophilic monomer material. Consequently, there is a need for a method of modifying the character of the hydrophobic surface of the casting mould in order to improve the acceptability of the hydrophilic pigment carrier applied to the surfaces.

Numerous methods of achieving this are known in the art, for example, the surfaces of many types of plastic articles such as photographic film, automobile body parts, laminated sheets, packaging films, floor covering materials, plastic bottles and the like, have been subjected to different types of hydrophilizing treatment, such as glow discharge, surface plasma treatment, electric corona discharge, direct or alternating current discharge, microwave discharge, and the like, in order to enhance the ability of the articles to accept adhesives, coatings, paint, printing ink, and the like. A representative list of U.S. patents dealing with this subject includes U.S. Pat. Nos. 3,428,801; 3,888,753; 3,944,709: 4,275,301; 4,467,200; 4,719,533; 4,724,508; and 4,854,999.

Previously, the foregoing technology has not been used for the treatment of casting moulds. The purpose of the technology is to bond materials firmly to the hydrophobic surface and thus prevent release of the materials therefrom, and, since one of the essential characteristics of a casting mould is that it be capable of releasing the moulded article upon completion of the process, the use of such technology has been contradictory.

Further, various chemical reagents, such as solvents, release agents, and reactant vapours, have been used to treat casting mould surfaces for various purposes (e.g. U.S. Pat. No. 4,150,073). However, these systems have not been suggested for modifying an hydrophobic surface of a casting mould to enhance the acceptability of a hydrophilic pigment carrier.

It is an object of the present invention to provide an improved method for producing contact lenses having a colour pattern simulating the iris of the human eye.

It is another object of the invention to provide a method for modifying the surface of a hydrophobic lens casting mould to enhance the adhesion of a hydrophilic monomer colouring dispersion without interfering with the release properties of said mould.

It is a further object of the invention to provide a method for applying a highly effective coloured printed pattern, such as an iris pattern, to an optical lens, using a single monomer or monomer combination as both pigment carrier and lens forming material.

It is a still further object to provide a method for treatment of a hydrophobic casting mould to enhance its ability to hold an optical lens while an optical surface is being generated thereon, without interfering with subsequent release of the lens from the mould.

It is yet another object to treat the surfaces of a two-part optical lens casting mould to promote selective retention of the lens on a designated part of said mould.

SUMMARY OF THE INVENTION

This invention is based on the surprising discovery that electrical discharge treatment, such as corona discharge, can be used to modify the surface characteristics of casting moulds made from polymeric materials and, in particular enhance the acceptability of hydrophilic monomers without interfering with the release characteristics of the material of the mould. It has been found that, by subjecting the surfaces of the casting mould with electrical corona discharge prior to applying a coloured polymeric dispersion to the mould surfaces, a number of manufacturing and end product enhancements are achieved. Thus, lenses manufactured using such treated moulds are essentially free from included bubbles and possess a superior coloured area having improved pattern durability, definition and resolution. Also, the treatment enables manufacturing techniques for selectively controlling adhesion of the lens to the mould, and consequent release therefrom, at desired points in an automated procedure.

In accordance with a first aspect of the present invention there is provided a method of producing a contact lens comprising the steps of treating the surface of a hydrophobic lens casting mould with electrical corona discharge, selecting an active material to be used in the lens, dispersing the active material in a hydrophilic carrier system which is compatible with said monomer material, using the resulting dispersion to coat the electrical corona discharge treated surface of the casting mold, introducing a hydrophilic monomer lens forming liquid into said mould in contact with the coated surface, polymerizing the liquid to produce a lens blank having the active material impregnated in said blank, adjacent an optical surface thereof, and subsequently removing the lens from the mold.

In accordance with the present invention the active material may be a colouring material or a therapeutic agent.

It has been found that the electrical corona discharge treatment used in accordance with the present invention can be used in a number of varying atmospheres, and that in fact the actual atmosphere used can have a marked and real effect on the end result of the treatment.

The use of the electrical corona treatment in an active atmosphere, i.e. an atmosphere which actively take part in an oxidation or reduction type reaction, can result in the surface under treatment undergoing such a reaction. In circumstances where the quality of the finish is of major importance this can lead to a deterioration in the quality of the final finished product, for example in the present application, the production of contact lenses, the electrical corona discharge treatment may cause reaction at the optical quality surface of the mould that is transferred to the finished optical surface of the contact lenses leading to a degradation of quality in the finished lens.

In a majority of applications this reaction characteristic is not critical, or of any significance and can consequently be ignored.

It is proposed that in a preferred embodiment of the present invention the electrical corona discharge treatment is carried out in an inert atmosphere with regard to the material of the casting mould under treatment, for example in an atmosphere of an inert gas such as nitrogen, argon or krypton.

In a particular embodiment of the present invention a method of producing a coloured contact lens comprises the steps of treating the surface of a lens casting mould with electrical corona discharge, selecting a colouring material which is insoluble in the monomer material to be used in the lens, dispersing said colouring material in a carrier system which is compatible with said monomer material, using the resulting dispersion to imprint a pattern on a surface of a casting mould, introducing a monomeric lens forming liquid in said mould in contact with said imprinted surface, polymerizing said liquid to produce a lens blank having a coloured pattern impregnated in said blank, adjacent an optical surface thereof, and subsequently removing said lens from said mould.

Clearly, the actual treatment of the surface of the lens casting mould is a subjective matter however, preferably the surface of the lens casting mould is treated with electrical corona discharge for a period of from 0.2 to 2.0 seconds. This is in order to ensure sufficient treatment of the surface, however prevent over-treatment, and breakdown of the polymeric material in the polymer surface of the mould, or destruction of the release properties of the mould. Further, these properties are also affected by the power of the treatment, preferably, therefore the surface of the lens casting mould is treated with electrical corona discharge of between 2 and 80 KV at an Hz value of between 50 and 500 Hz.

It has been mentioned above that the electrical corona treatment acts to bond material firmly to the hydrophobic surface and thus prevent release of the materials therefrom. The above discussion concerning the period of treatment and power of the treatment, and in particular the values given concern providing conditions under which adequate adhesion is given to enable a defined pattern to be given to the coat on the surface whilst enabling release of the cast contact lens without damage to the lens.

Previously, it has been proposed that the whole surface of the mould should be electrical corona discharge treated. However as will be well appreciated by those in the contact lens industry with certain types of contact lens the colouring dispersion is applied as a band of colour/coloured pattern which overlies the iris of the human eye. Therefore, there are sections of the casting mould surface which are treated to which the colour/coloured pattern are not applied, namely the section corresponding to the pupil of the eye, and with soft contact lenses a thin band surrounding the iris section.

Now it has been found that with certain lens casting formulations the adhesion of the cast lens to the mould surface is sufficient to cause cracking to the cast contact lens upon attempted release. In certain circumstances this may cause in the order of 50-60% of the lenses to be rejected. Clearly, in any manufacturing operation a rejection factor so high is completely unacceptable.

Therefore in a preferred embodiment of the present inventions area sections of the mould surface whose area are within the area of the surface which corresponds to the pupil of the contact lens or the periphery surrounding the section to which the colouring-/coloured pattern is applied are masked during the electrical corona discharge treatment of the surface.

The masking of the mould surface prevents the electrical corona discharge treatment reaching areas of the mould surface, and consequently the enhanced adhesion property brought about by the treatment is not present in these areas. When the surface is looked at as a whole the result of this is to reduce the adhesive forces and thereby enable easier release of the cast contact lens. Further resulting from the fact that less force has been utilised there is less chance that the cast contact lens will be damaged.

As will be well appreciated by those in the industry, lens casting moulds come in two mutually cooperating halves; a male member and a female member, preferably the masking is achieved by means of an adapted cooperating mould half to the mould half being treated.

Preferably, the contact lens made by the method in accordance with the present invention is a soft contact lens and therefore the monomer is a hydrogel-forming material, and, most preferably, hydroxyethyl methacrylate.

Preferably, the carrier system for the colourant comprises a monomeric hydrogel forming material, and, most preferably, a monomeric hydrogel forming material which is the same as the hydrogel-forming material from which the lens is to be made.

The colouring material dispersed in the carrier system may comprise a suitable pigment in particulate form, for example, titanium dioxide, phthalocyanine blue, phthalocyanine green, or a mixture containing one or more of titanium dioxide, phthalocyanine blue and phthalocyanine green.

In accordance with one particular embodiment of the present invention a method of producing a coloured contact lens comprises the steps of treating the surface of a hydrophobic casting mould with electrical corona discharge, preparing a colouring dispersion comprising from 10 to 90% by weight of a colouring material which is insoluble in hydroxyethyl methacrylate, using the said dispersion to imprint a pattern on a surface of said treated casting mould, introducing additional hydroxyethyl methacrylate monomer in said mould in contact with said imprinted surface, polymerizing said monomer to produce a lens blank having a coloured pattern impregnated in said blank, adjacent an optical surface thereof, and subsequently removing said lens from said mould.

Preferably, in this particular embodiment the colouring dispersion comprises from 60 to 80% hydroxyethyl methacrylate monomer, from 1 to 25% titanium dioxide, from 0.01 to 5% phthalocyanine blue, from 0.01 to 3% black iron oxide, and from 1 to 5% fumed silica.

Once the lens blank has been removed from the mould preferably said lens blank is subsequently hydrated and finished to produce a coloured soft hydrogel lens.

In accordance with a second aspect of the present invention a method for producing a coloured contact lens comprising the steps of treating the surface of a hydrophobic lens casting mould with electrical corona discharge, preparing a colouring dispersion comprising from 10 to 90% by weight of monomeric hydroxyethyl methacrylate and from to to 90% by weight of a colouring material which is insoluble in hydroxyethyl methacrylate, using the said dispersion to imprint a pattern on a surface of the treated casting mould, introducing additional hydroxyethyl methacrylate monomer in said mould in contact with the imprinted surface, polymerizing the monomer to produce a lens blank having a coloured pattern impregnated in said blank, adjacent an optical surface thereof, and subsequently removing the lens from the mould.

In accordance with a third aspect of the present invention a method of producing a contact lens in a two part mould system having a first part and a second part, comprising the steps of treating a surface of said first part, but not said second part, with electrical corona discharge, introducing a monomeric lens forming liquid in said mould, and polymerizing said liquid to produce a lens blank, whereby upon separation of said first part from said second part, said lens is selectively retained on said first part.

It has been further discovered that, improvements in the quality of the lens manufactured in accordance with the present invention can be obtained even in the production of clear contact lenses, if the hydrophobic casting mould is treated with corona discharge prior to introduction of the hydrophilic lens forming monomer into the mould.

The corona treatment substantially reduces the formation of bubbles in the finished lens.

Further, the corona treatment provides increased adhesion of the lens to the mould, so the mould containing the lens may be placed in a lathing mandrel and an optical surface generated on the lens while it is held securely in the mould. However, the adhesive force is not so great as to interfere with desired release of the lens from the mould when the lathing operation is complete.

Utilizing the same discovery, the invention provides a method for causing a lens formed between two mould halves to adhere preferentially to only one of the mould halves. Thus, by treating only one of the mould halves with corona discharge, it has been found that, upon opening the mould after polymerization of the lens forming monomer, the lens adheres selectively to the treated half, thereby enhancing the ease and efficiency of an automated manufacturing procedure.

The invention also comprises an improved method, utilizing corona discharge treatment, for producing an optical lens having an active material other than a colouring pigment impregnated in the lens, adjacent to one or both optical surfaces thereof. For the purposes of this specification, the term "active material" includes (1) insoluble materials that provide colour in the lens or a means of controlling radiation, such as UV radiation or (2) soluble therapeutic agents.

DETAILED DESCRIPTION OF THE INVENTION

Figure 1:
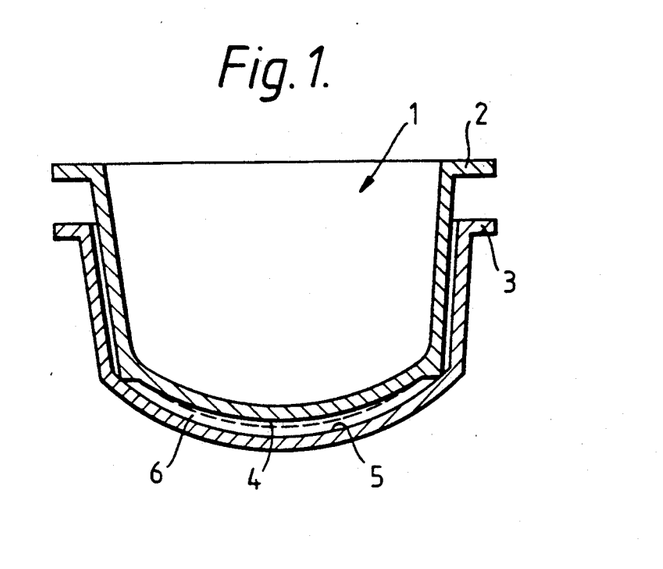
FIG. 1 shows a contact lens casting mould.

Now referring to FIG. 1 of the accompanying drawings there is shown a mould 1 comprising a pair of contact lens mould halves 2,3, suitable for use with the method of the present invention. The mould halves shown in this figure are fully described in the specification of U.S. Pat. No. 4,955,580 and consequently only a brief description is given here.

The mould half 2 comprises the male mould member of the mould and has a surface 4 which defines one of the optical surfaces of a cast contact lens.

The mould half 3 comprises the female mould member of the mould and has a surface 5 which defines one of the optical surfaces of a cast contact lens.

When in an assembled condition, as shown in the figure, the male member and female member interrelate so that a space 6 is defined which space is bordered by the surfaces 4 and 5 of the respective mould halves.

Figure 2:
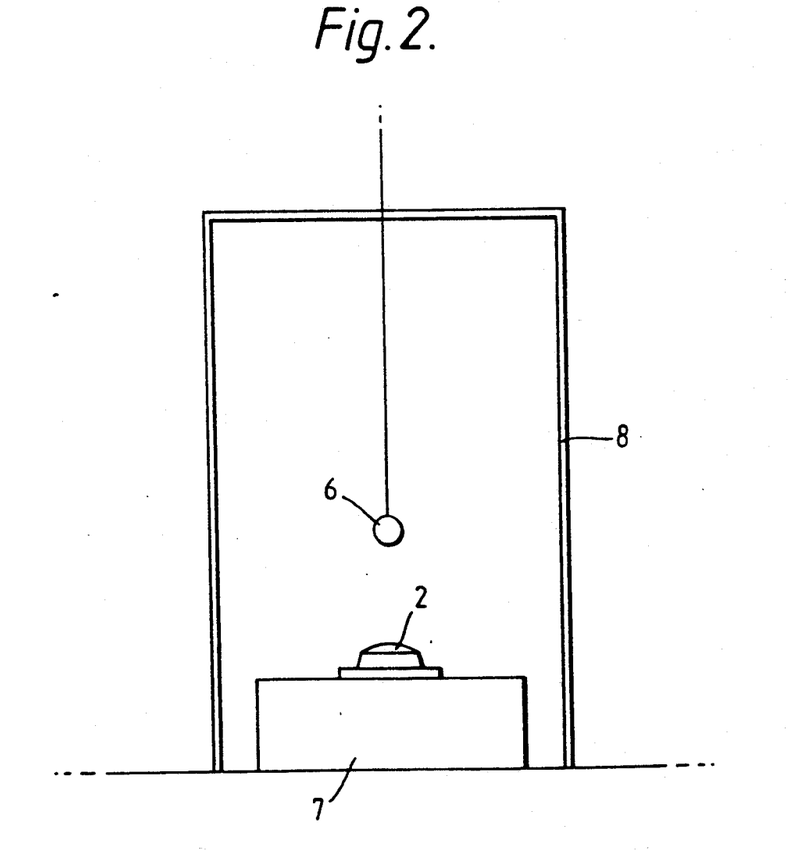
FIG. 2 shows a schematic view of an electrical corona discharge treatment apparatus.

Now referring to FIG. 2 of the accompanying drawings, there is shown a schematic representation of the electrical corona discharge treatment apparatus, for example a Model HVO5 of Tantec Inc.

The apparatus includes a ball type electrode 6 and a support station 7 onto which the mould half to be treated is placed for treatment. The ball type electrode bulb 6 and support station 7 are enclosed in a casing 8.

In use the ball type electrode bulb 6 is in close proximity to the surface of the mould half which is to be treated. The electrical potential between the ball type electrode bulb 6 and the surface to be treated is increased leading to the treatment of the surface. The treatment is witnessed by the discharge glow about the surface under treatment.

In the particular case illustrated in FIG. 2 of the accompanying drawings it is the optical/convex surface of the male inserted member 2 which is undergoing treatment. This is not intended to be limiting to the present application as the optical/concave surface of the female member 3 can be easily treated.

Figure 3:
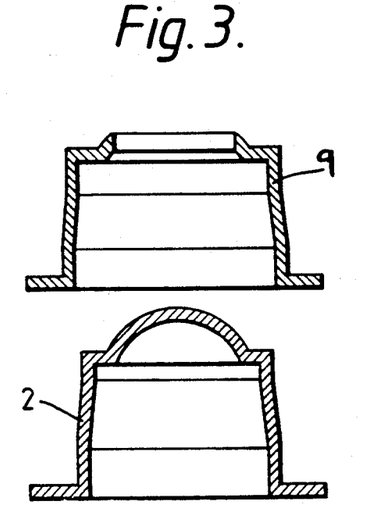
FIG. 3 shows a masking arrangement for use with the present invention.
Figure 4:
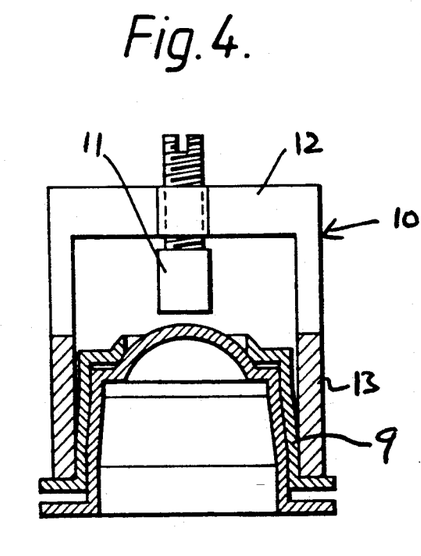
FIG. 4 shows a second masking arrangement for use with the present invention.

Now referring to FIGS. 3 and 4 of the accompanying drawings there is shown a masking arrangement for use with the present invention. The masking arrangement is normally used in situations where the surface area of the surface undergoing treatment is to be reduced/limited in order to reduce the adhesive effects caused by the treatment and enable easier release of the cast contact lens, and thereby reduce the likelihood of damage to the finished lens.

The basic masking arrangement as shown in FIG. 3 comprises a shield member 9. In the arrangement shown the shield member 9 is designed to mask out some of area of the optical surface of the male mould member of a contact lens mould 1 which does not require treatment. In the simple form of the mask illustrated a female mould member 3 has been adapted by removing material where appropriate so that when it is placed over the male mould member, the surface area of the optical surface 4 which is to be treated is exposed.

FIG. 4 of the drawings illustrates a second form of masking arrangement in accordance with the present invention. In this particular case the masking arrangement described with reference to FIG. 3 of the accompanying drawings is utilised, and in addition a second member 10 having a downwardly projecting member 11 is provided.

The second member 10 and downwardly projecting member 11 do not significantly affect the corona discharge flow to the areas where the electrical corona discharge treatment is desired.

The second member 10 comprises:
- a circumferentially extending skirt 13 which engages with the shield member 9 and holds said shield member in position whilst locating the second member, and
- an upwardly projecting diametrically disposed bridge member 12 from which the downwardly projecting member 11 is disposed.

The downwardly projecting member 11 is in fact in the form of a plastic screw which is arranged so that the screw's head acts to mask a central zone of the male mould member 2 from electrical corona discharge treatment. This central zone will in this particular example correspond to the pupil zone of a finished contact lens.

In use the masking arrangement along with the male mould member 2 are dispersed on the support station 7 for treatment.

In accordance with the present invention, the first step in the methods involves applying an electrical corona discharge treatment to the optical surface of the male mould member 2 of a casting mould which is to be used to form a contact lens. The male mould member 2 may have the optical surface treated as a whole, or a masking arrangement used to limit the exposure of the optical surface.

It has been found that an effective treatment to a surface is provided with a corona discharge of 27 KV at 22 Hz for a period of from 0.2 to 2.0 seconds. If such corona discharge continues for longer than 2.0 seconds, the adhesion of the finished lens to the mould begins to increase, and eventually it becomes difficult or impossible to remove the finished lens from the mould. Therefore, for the power of the discharge given above it is desired to maintain the time of treatment between 0.2 to 2.0 seconds in order to obtain the proper balance of lens quality and release properties, although it will be understood that the time of treatment may be extended outside this range by modifying the intensity of the corona discharge treatment.

The invention is particularly applicable to casting moulds made from a hydrophobic material such as polyethylene, polypropylene or other polyolefins, although any casting mould material whose wettability is increased by the corona discharge treatment may be used to advantage.

When the mould has been treated with corona discharge, it is ready for imprinting of a pattern on its treated surface. The special colouring liquid, or ink, which is used for the imprinting is prepared by dispersing an insoluble pigment or dye in a carrier system, and the desired pattern is applied to the treated mould surface by printing techniques, such as pad transfer printing.

The invention is particularly useful when the carrier system for the colouring material is a hydrophilic monomer of the type from which the contact lens itself is made. For example, if the lens is to be made from a hydroxyethyl methacrylate monomer, there are substantial compatibility advantages if the carrier for the insoluble colouring material is also a hydroxyethyl methacrylate monomer. A description of the many hydrophilic monomers which may be used as the pigment carrier system (and also as the lens forming material) is included hereinafter in this specification at the point where production of the lens is described.

The carrier system as described is mixed with the colouring material to prepare a suitable dispersion. The colouring material may be any colourant which is insoluble in the monomer to be used to form the lens. Preferred colourants include phthalocyanine blue, phthalocyanine green, chromic-alumina-cobaltous oxide, chromium oxides, and various iron oxides for red, yellow, brown and black colours. Opaquing agents such as titanium dioxide may also be included. For most applications, it is desirable to employ a mixture of colours, for better simulation of natural iris appearance. Although pigments are the preferred form of colourant, it is also possible to use dyes which are insoluble in the monomer lens material and which can be dispersed in the carrier.

The concentration of the colourant added to the carrier system is governed by the intensity and type of the colourant. The objective is to add sufficient pigment or dye to give optimum hiding power when applied in a printing film thickness of about 10 to 40 microns. Generally, the colourant may be added in concentrations of about 1 to 80% by weight of the carrier.

The dispersion of the colourant in the carrier system is achieved by conventional means, such as vigorously mixing in a high speed blender or milling in a roll or ball mill or by use of an ultrasonic probe. The milling and dispersion are continued until the mixture is uniform and the size of the particles has been reduced to 10 microns or below. The addition of ingredients and the dispersing techniques are carried out with the objective of preparing a printing ink with suitable viscosity for use in the subsequent offset printing oepration. If necessary, conventional thixotropic agents can be added at this stage to provide the necessary sag resistance, or otherwise impart a thixotropic index sufficiently high to prevent running of the ink when subsequently applied to the surface of the casting mould.

As the next step, the above printing dispersion is used to imprint a pattern (such as that of the iris) on the corona discharge treated surface or surfaces of the casting mould which is to be used for producing the lens. The pattern is created by etching on a steel plate using well known etching techniques, and then a commercially available pad transfer printing machine is used to apply the pattern to the mould surface. The pattern on the steel plate may be generated by computer design and consists of an arrangement of etched impressions, in which the intensity of the finished colour may be controlled by the frequency and depth of the impressions. The etching is accomplished by applying to the steel plate a solution of material which insolubilizes when exposed to light; covering the plate with the pattern matrix; exposing the plate to light to insolubilize the areas not covered by the pattern; washing away the soluble areas; and then etching the remaining areas to the desired depths.

In the operation of the pad transfer printing machine, a doctor blade smears the ink on the steel plate, and then a silicone pad is applied to pick up the ink pattern and transfer it to the corona treated surface of the casting mould. If desired, the printing procedure may be repeated using different colours or different patterns, to achieve the desired colour or intensity. It is understood that the pattern may also be applied to the mould surface by other printing techniques, such as jet spray, silk screen or laser printing including liquid crystal shutters.

When the pattern has been imprinted on the corona discharge treated casting mould surface or surfaces, as above, the monomer to be used to form the lens is then poured into the mould, together with suitable conventional curing initiators. It is a feature of the present invention that, when the monomer is thus introduced, it causes a mechanical altering and softening of the surface of the individual colourant capsules, which allows the monomer to penetrate the interstices between the capsules and surround them, so that the capsules become impregnated in the monomer matrix with the pattern remaining intact. As an extension of this phenomenon, a thin layer of monomer interposes itself between the colourant capsules and the casting mould surface, so that when the finished lens is subsequently removed from the mould, the surface is a substantially intact layer of lens forming material, with the printed pattern of colourant capsules located beneath said surface, but closely adjacent thereto.

The monomer casting liquid which is poured into the mould as above may be any of the conventional monomers or mixtures thereof which are known in the art for the production of plastic contact lenses. For example, in the area of soft contact lenses, the hydroxyethyl methacrylate and ethylene glycol dimethacrylate monomer mixtures described in U.S. Pat. No. 2,976,576 and U.S. Pat. No. Re. 27,401 may be used, as well as the hydroxyalkyl methacrylates and vinyl pyrrolidone described in U.S. Pat. No. 3,503,393. Specific suitable monomer materials include 2-hydroxyethyl methacrylate, 2-hydroxypropyl acrylate, glycerol methacrylate, glycidyl methacrylate, dimethylaminoethyl methacrylate, acrylic acid, methacrylic acid, collagen, acrylamide, diacetone acrylamide, and the like. Included also are monomeric materials resulting in polymers such as tefilcon, phemfilcon, hefilcon A, hefilcon B, perfilcon A, lidofilcon B, tetrafilcon A, droxifilcon A, ocufilcon B, Bufilcon A, crofilcon A, deltafilcon A, natrafilcon A, and etafilcon A. These are United States approved drug names (USAN).

The lens forming monomer may also be selected from the type used to produce rigid lenses, particularly gas permeable rigid lenses. Examples include hydrophobic acrylic-type polymers such as polymethyl methacrylate. The lens forming monomer may also be selected from elastomeric materials such as polysiloxane.

As the next step, polymerization of the monomer liquid is initiated and completed under appropriate known curing conditions, which include curing in an oven or the use of other techniques such as radiation, including UV and microwave, or the use of a bath with a heat transfer fluid, such as water and silicone oil.

Following this, the lens is dismounted from the mould and then finished in the usual fashion. In the case of soft hydrogel lenses, the finishing will include customary hydrating techniques. Finally, the lens is scrutinized by quality control procedures, and the final product is then ready for packing and labelling.

It is a feature of the invention that corona discharge treatment of the casting mould surface produces finishes lenses which are essentially free from included bubbles and possess a superior coloured area having improved pattern durability, definition and resolution. It is a further feature of the invention that, although the corona discharge treatment used in the process has been known in the art for permanently fixing coatings, adhesives, inks, and the like, the treatment of the present invention provides a balanced adhesion, in which the adhesive forces provide certain product and process enhancements but do not interfere with the essential mould release characteristics at the end of the process.

Thus, if it is desired to form lenses from cast moulding between two mould halves, and to cause the finished lens to be preferentially adhered only to one half of the mould for further treatment, this can be readily accomplished by use of the present invention by corona discharge treatment of only the mould half to which adhesion is desired.

Alternatively if the lens is being prepared by a technique in which only one optical surface is produced in a casting mould, and the other surface prepared by lathing, the technique of the present invention can be utilized by applying the corona discharge treatment to the single surface utilized in the casting mould. Then, when the lens has been formed, the mould can be placed in a lathing mandrel and the second surface of the lens generated while the lens is still held securely in the casting mould. The corona discharge treatment affords secure adhesion of the lens to the mould while the lathing operation is carried out, but does not prevent release of the lens from the mould at the appropriate time.

Further, it was discovered in the course of work with the invention that, even in the production of clear lenses, not involving the imprinting of a colour pattern, the quality of the lens is improved if the hydrophobic casting mould is treated with corona discharge prior to introducing the hydrophilic lens forming monomer into the mould. Clear lenses formed in this manner are essentially bubble free and are substantially improved in terms of optical definition and reproducibility.

The procedure described above may also be used to place a layer of an aqueous soluble therapeutic agent or an encapsulated aqueous soluble therapeutic agent, rather than or in addition to the coloured layer, adjacent to the surface of a soft contact lens. The system may be designed to provide for the optimum controlled and prolonged release of the therapeutic agent. Such therapeutic agents include, but are not limited to, pilocarpine, epinephrine, chromolyn sodium and idoxuridine.

The following examples describe specific embodiments which are illustrative of the invention but should not be interpreted as limiting the scope of the invention in any manner. All parts and percentages are by weight unless otherwise specified.

EXAMPLE 1

A coloured monomer mix is prepared by dispersing 20 weight percent titanium dioxide, 4 weight percent phthalocyanine blue, 2 weight percent black iron oxide and 4 weight percent fumed silica into 70 weight percent hydroxyethyl methacrylate. A polyolefin lens casting mold is subjected to corona discharge of 28 KV at 22 Hz for 1 second. The coloured mix is then applied to the treated area of the polyolefin mould surface in a highly defined pattern using a pad transfer printing apparatus. A lens monomer mix prepared from 99.3 weight percent hydroxyethyl methacrylate, 0.5 weight percent ethyleneglycol dimethacrylate and 0.2 weight percent benzoin methyl ether is then added to the lens mould, and the whole is polymerized under ultraviolet light of 365 nm. After polymerization and demoulding, a lens with a desired coloured pattern is obtained. The lens is then finished through the routine processing steps and hydrated and packaged.

When the coloured mix is applied to a polyolefin casting mould without prior exposure to corona discharge, the printed pattern immediately beads up to form an unrecognizable pattern with no spreading of the coloured mix.

EXAMPLE 2

Lenses are prepared by use of the procedure in Example 1, but with varying time of exposure to the corona discharge treatment. The print quality and the lens release characteristics for the various times of exposure are given in the table below:

| Lens No. | Exposure Time (Seconds) | Print Quality | Lens Release |
| --- | --- | --- | --- |
| 1 | 0 | Very poor, pronounced beading | Good |
| 2 | 0.2 | Fair | Good |
| 3 | 0.5 | Good | Good |
| 4 | 1.2 | Excellent | Fair to good |
| 5 | 2.0 | Excellent | Hard |
| 6 | 4.0 | Excellent | Difficult |
| 7 | 5.0 | Excellent | Impossible |

EXAMPLE 3

A polyolefin mould is exposed to a corona discharge as per Example 1 for 1 second and is then printed according to Example 1. The printed monomer layer is allowed to dry and is then re-exposed to a second corona discharge for 1 second. The polyhydroxyethyl methacrylate lens is then prepared as per Example 1. After hydration of the lens it is immersed in an aqueous solution of 50% methanol. The swollen lens is then rubbed vigorously between the finger and palm of the hand. After this testing the lens was examined and found to have retained all of the coloured material and in this sense was an improvement over the lens of Example 1, which tended to lose some of the coloured pattern when subjected to a similar test.

EXAMPLE 4

Polyolefin lens moulds are exposed to a corona discharge of 28 KV at 22 Hz for 0.7 seconds. Clear polyhydroxyethyl methacrylate lens is prepared from the moulds using a monomer mix of 99.3 weight percent hydroxyethyl methacrylate, 0.5 weight percent ethylene glycol dimethacrylate and 0.2 weight percent di(4-tert-butylcyclohexyl) peroxydicarbonate. The lenses are polymerized by heating at 60 degrees Centigrade for 10 hours. Lenses formed in this manner were free from included bubbles, whereas lenses prepared from moulds that were not exposed to corona discharge contained varying degrees of bubbles.

EXAMPLE 5

Following the procedure set forth in Example 4, polyhydroxyethyl methacrylate lenses were prepared in polyolefin moulds that had been exposed to corona discharge for various times. The results of exposure times on the properties of the lenses are given in the table below:

| Lens No. | Exposure time (Seconds) | Lens Quality | Lens Release |
| --- | --- | --- | --- |
| 1 | 0 | Bubbles in lens | Good |

-continued

| Lens No. | Exposure time (Seconds) | Lens Quality | Lens Release |
|---|---|---|---|
| 2 | 0.2 | No bubbles, good lenses | Good |
| 3 | 0.5 | Some cracked lenses, no bubbles | Good |
| 4 | 1.0 | No bubbles | Good |
| 5 | 1.5 | Broken lenses | Poor |
| 6 | 2.0 | Chipped, broken | Very hard |
| 7 | 4.0 | Not salvageable | Very difficult |
| 8 | 5.0 | Not salvageable | Impossible |

EXAMPLE 6

The male mould of a two part polyolefin lens moulding system is exposed to a corona discharge of 28 KV at 22 Hz for 0.7 seconds. Lenses are produced from a mixture of 99.3 weight percent hydroxyethyl methacrylate, 0.5 weight percent ethylene glycol dimethacrylate, and 0.2 weight percent benzoin methyl ether. The lenses are polymerized by exposure to ultraviolet irradiation. After polymerization and upon splitting the male and female mould halves apart, it was found that all of the lenses adhered to the male half of the mould. Likewise, when the female mould halves only were similarly exposed to the corona discharge, all the lenses were selectively retained in the female half of the mould upon opening.

EXAMPLE 7

The inside surface of a polyolefin mould, designed to be collected in a lathe and to hold monomer mix in a supported cup containing a convex base, is exposed to a corona discharge of 28 KV at 22 Hz for 0.7 seconds. A monomer mix of 99.3 weight percent hydroxyethyl methacrylate, 0.5 weight percent ethylene glycol dimethacrylate and 0.2 weight percent benzoin methyl ether is added to the cup, and the whole is exposed to UV irradiation to polymerize the material. Upon polymerization of the material, the mould is held in a lathe and the material is cut down to produce a thin hemispherical shell (lens), with the base forming one surface of the lens. While the material was sufficiently adhered to the polyolefin mould to allow machining of the lens, the finished lens nevertheless could be easily removed from the mould.

Although various preferred embodiments of the invention have been described herein in detail, it will be understood by those skilled in the art that variations may be made thereto without departing from the spirit of the invention.

What is claimed is:

1. The method of producing a contact lens comprising the steps of treating a surface of a hydrophobic lens casting mould with electrical corona discharge, selecting an active material which is insoluble in the monomer material to be used in the lens, dispersing said active material in a hydrophilic carrier system which is compatible with said monomer material, using the resulting dispersion to coat the electrical corona discharge treated surface of said casting mould, introducing a hydrophilic monomeric lens forming liquid in said mould in contact with said coated surface, polymerizing said liquid to produce a lens blank having an active material impregnated in said blank, adjacent an optical surface thereof, and subsequently removing said lens from said mould.

2. The method of claim 1 in which the active material is a colouring material.

3. The method of claim 1 in which the active material is a therapeutic agent.

4. The method of claim 1 in which said carrier system comprises a monomeric hydrogel forming material.

5. The method of claim 1 in which said lens casting mould is made from a polyolefin material.

6. The method of claim 1 in which, area sections of the mould surface, whose area are within the area of the surface which corresponds to the pupil of the contact lens or the periphery surrounding the section to which the colouring/coloured pattern is applied, are masked during the electrical corona discharge treatment of the surface.

7. The method of producing a coloured contact lens comprising the steps of treating the surface of a lens casting mould with electrical corona discharge, selecting a colouring material which is insoluble in the monomer material to be used in the lens, dispersing said colouring material in a carrier system which is compatible with said monomer material, using the resulting dispersion to imprint a pattern on a surface of a casting mould, introducing a monomeric lens forming liquid in said mould in contact with said imprinted surface, polymerizing said liquid to produce a lens blank having a coloured pattern impregnated in said blank, adjacent an optical surface thereof, and subsequently removing said lens from said mould.

8. The method of claim 7 in which the surface of said lens casting mould is treated with electrical corona discharge for a period of from 0.2 to 2.0 seconds.

9. The method of claim 7 in which the surface of the lens casting mould is treated with electrical corona discharge of between 2 and 80 KV at an Hz value of between 22 and 500 Hz.

10. The method of claim 7 in which said lens casting mould is made from a polyolefin material.

11. The method of claim 7 in which said pattern is an iris pattern.

12. The method of claim 7 in which the monomer is a hydrogel-forming material.

13. The method of claim 7 in which said carrier system comprises a monomeric hydrogel forming material.

14. The method of claim 7 in which said carrier system comprises a monomeric hydrogel forming material which is the same as the hydrogel-forming material from which the lens is to be made.

15. The method of claim 7 in which the monomer is a hydroxyethyl methacrylate.

16. The method of claim 7 in which the colouring material is titanium dioxide.

17. The method of claim 7 in which the colouring material is phthalocyanine blue.

18. The method of claim 7 in which the colouring material is phthalocyanine green.

19. The method of claim 7 in which the colouring material is a mixture of titanium dioxide, phthalocyanine blue and phthalocyanine green.

20. The method of claim 7 in which, area sections of the mould surface, whose area are within the area of the surface which corresponds to the pupil of the contact lens or the periphery surrounding the section to which the colouring/coloured pattern is applied, are masked during the electrical corona discharge treatment of the surface.

21. The method of producing a coloured contact lens comprising the steps of treating the surface of a hydrophobic casting mould with electrical corona discharge, preparing a colouring dispersion comprising from 10 to 90% by weight of monomeric hydroxyethyl methacrylate and from 10 to 90% by weight of a colouring material which is insoluble in hydroxyethyl methacrylate, using the said dispersion to imprint a pattern on a surface of said treated casting mould, introducing additional hydroxyethyl methacrylate monomer in said mould in contact with said imprinted surface, polymerizing said monomer to produce a lens blank having a coloured pattern impregnated in said blank, adjacent an optical surface thereof, and subsequently removing said lens from said mould.

22. The process of claim 21 in which the colouring dispersion comprises from 60 to 80% hydroxyethyl methacrylate monomer, from 1 to 25% titanium dioxide, from 0.01 to 5% phthalocyanine blue, from 0.01 to 3% black iron oxide, and from 1 to 5% fumed silica.

23. The process of claim 21 in which the pigment particles are less than 5 microns in size.

24. The process of claim 21 in which the said lens blank is subsequently hydrated and finished to produce a coloured soft hydrogel lens.

25. The method of claim 21 in which, area sections of the mould surface, whose area are within the area of the surface which corresponds to the pupil of the contact lens or the periphery surrounding the section to which the colouring coloured pattern is applied, are masked during the electrical corona discharge treatment of the surface.

26. The method of producing a contact lens comprising the steps of treating a surface of a lens casting mould with electrical corona discharge, selecting an active material which is insoluble in the monomer material to be used in the lens, dispersing said active material in a carrier system which is compatible with said monomer material, using the resulting dispersion to coat the corona discharge treated surface of said casting mould, treating the coated surface of said lens casting mould with further electrical corona discharge, introducing a monomeric lens forming liquid in said mould in contact with said coated surface, polymerizing said liquid to produce a lens blank having an active material impregnated in said blank, adjacent an optical surface thereof, and subsequently removing said lens from said mould.

27. The method of producing a contact lens comprising the steps of treating a surface of a lens casting mould with electrical corona discharge, selecting a colouring material which is insoluble in the monomer material to be used in the lens, dispersing said colouring material in a carrier system which is compatible with said monomer material, using the resulting dispersion to imprint a pattern on a surface of said casting mould, introducing a monomeric lens forming liquid in said treated mould, polymerizing said liquid to produce a lens blank having a first optical surface thereon and a colour pattern impregnated therein, generating a second optical surface on said blank while said casting mould containing said blank is mounted on a precision mandrel, and subsequently removing said lens from said mould.

* * * * *